United States Patent
Hauser et al.

[11] Patent Number: 5,549,692
[45] Date of Patent: Aug. 27, 1996

[54] TWO-PART HIPJOINT SOCKET FOR ANCHORING IN THE PELVIC BONE

[75] Inventors: René Hauser, Zollikon; Yvan Sandoz, Winterthur, both of Switzerland

[73] Assignees: Sulzer Medizinaltechnik AG, Winterthur; Allo Pro AG, Baar, both of Switzerland

[21] Appl. No.: 257,214

[22] Filed: Jun. 8, 1994

Related U.S. Application Data

[63] Continuation of Ser. No. 986,162, Dec. 3, 1992, abandoned.

[30] Foreign Application Priority Data

Jan. 16, 1992 [CH] Switzerland .................. 00112/92

[51] Int. Cl.$^6$ .................................................. A61F 2/34
[52] U.S. Cl. .............................. 623/22; 623/18
[58] Field of Search ..................... 623/22, 23, 18

[56] References Cited

U.S. PATENT DOCUMENTS

| | | | |
|---|---|---|---|
| 4,878,918 | 11/1989 | Tari et al. | 623/22 |
| 4,961,748 | 10/1990 | Frey et al. | 623/22 |
| 5,176,711 | 2/1993 | Grimes | 623/18 |
| 5,192,329 | 3/1993 | Christie et al. | 623/22 |

FOREIGN PATENT DOCUMENTS

| | | | |
|---|---|---|---|
| 0402810 | 12/1990 | European Pat. Off. | |
| 2578162 | 9/1986 | France | 623/22 |
| 2633509 | 1/1990 | France | |
| 3205527 | 8/1983 | Germany | |
| 1123682 | 11/1984 | U.S.S.R. | 623/22 |
| 1627171 | 2/1991 | U.S.S.R. | 623/23 |

*Primary Examiner*—David Isabella
*Attorney, Agent, or Firm*—Townsend and Townsend and Crew

[57] ABSTRACT

A hipjoint socket having a metal outer shell (1) which may be anchored in the pelvis. The shell (1) includes regions (3) of greater wall thickness (D) alternating in the circumferential direction with regions (4) of less wall thickness (d). The regions (3) of greater wall thickness (D) are made as guideshoes for supporting bodies (11) which may be slid onto them. The supporting bodies (11) are fixed to and, if necessary, positioned exactly on the aforesaid regions (3) with fixing members (13). A number of supporting bodies, (11) which may differ in shape and dimensions, are associated with each shell (1).

14 Claims, 3 Drawing Sheets

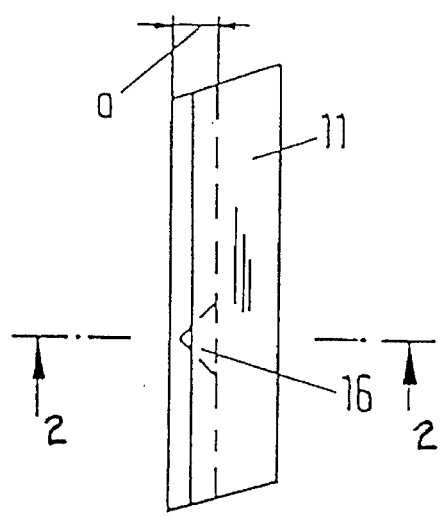
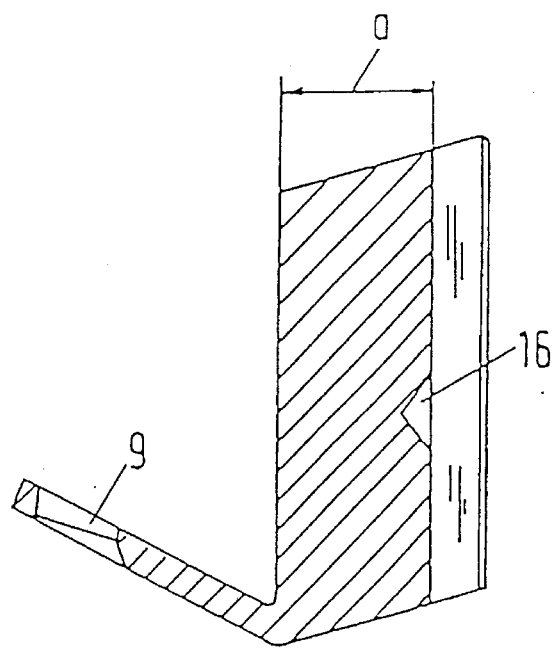
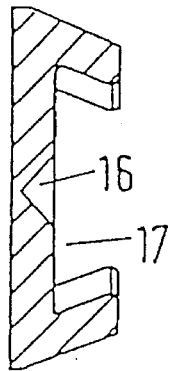
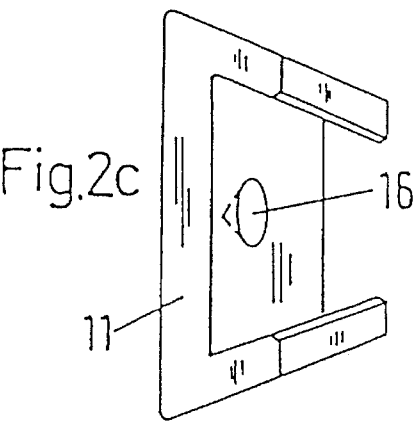
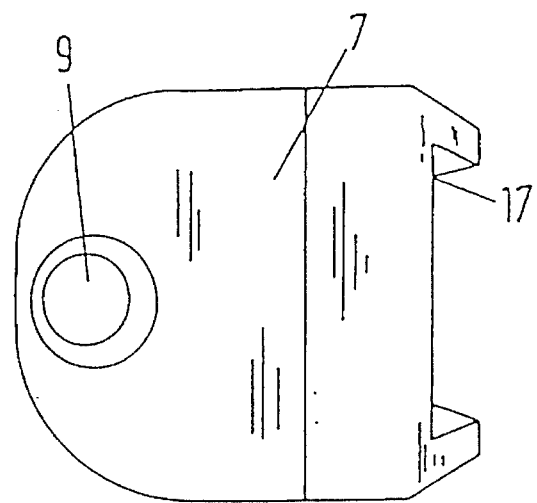

TWO-PART HIPJOINT SOCKET FOR ANCHORING IN THE PELVIC BONE

This is a Continuation of application Ser. No. 07/986,162, filed Dec. 3, 1992, now abandoned.

BACKGROUND OF THE INVENTION

The invention is concerned with a two-part hipjoint socket for anchoring in the pelvic bone. The hipjoint socket comprises a frustoconical shell and an insert which contains the actual cup of the socket and may be pressed with a snug fit into the hollow inside the shell. The shell is manufactured from metal and exhibits regions of greater wall thickness which alternate in the circumferential direction with regions having a smaller wall thickness. The regions having less thickness of wall are in cross-section sectors of a circular ring. While the regions of greater wall thickness have cress-section essentially trapezoidal which tapers in conically towards the pole.

A hipjoint socket of the kind named above is known from the U.S. Pat. No. 4,961,748. If this known socket has to be replaced during further operations, the difficulty very frequently occurs for the operating surgeon that for stable anchoring of the "spare" socket there is no longer enough bone substance round the hollow created operatively in the pelvis for the socket.

The problem of the present invention is so to enlarge the aforesaid known socket that on the one hand its basic conception which has stood the test may be preserved even in the case of the described lack of bone substance in the pelvis and on the other hand a firm anchoring of the "spare" socket is achieved. Obviously the invention is not restricted to cases of re-operation, but is still applicable even if the necessary bone substance is lacking in the pelvis for anchoring a socket.

SUMMARY OF THE INVENTION

This problem is solved by the present invention because the regions of greater wall thickness are made as guideshoes extending along the surface of the truncated cone for supporting bodies which may be slipped on externally, and that each of these regions is provided with fixing members for these supporting bodies.

In that case there is associated with each shell a kit of assorted supporting bodies which have different dimensions—e.g., different thicknesses—and/or have different shapes—e.g. increasing or decreasing in thickness steadily from the end next the base or in the form of a step. From this kit the operating surgeon can then choose one or more supporting bodies to suit the individual case, slide the chosen supporting bodies onto the shell and fix them to it by means of the fixing members.

As the connection between the shell and the supporting bodies it has stood the test if the supporting bodies have recesses like dovetails which embrace the trapezoidal cross-section of the regions and may be slipped onto the guideshoes from the pole.

By way of example setscrews which have conical centering tips and pass through the regions of greater wall thickness are a suitable kind of fixing member. If the setscrews engage in the supporting bodies in hollow conical recesses adapted to their centering tips, besides fixing the supporting body an exact positioning of it relative to the shell is achieved at the same time.

For additional bearing of the socket against the pelvic bone at least some of the supporting bodies may be provided at their ends next the base of the truncated cone with flaps pointing outwards, which furthermore for better fixing of the socket may have holes drilled in them for bone screws to pass through.

Growth of bone tissue or the adhesion between bone cement and the shell or the supporting bodies may finally be promoted if the regions of the shell having greater wall thickness and/or the supporting bodies are provided on their outer surfaces with sets of transverse teeth.

The invention is explained in greater detail below with the aid of embodiments in connection with the drawing.

BRIEF DESCRIPTION OF THE DRAWING

FIGS. 2a to 2c—reproduce a first embodiment of a supporting body, where 2a is a side elevation, 2b represents a section B—B from 2a, and 2c reproduces a view in the direction of the arrow C shown in 2a, of the endface associated with the base of the truncated cone;

DESCRIPTION OF THE PREFERRED EMBODIMENTS

Figure 1:
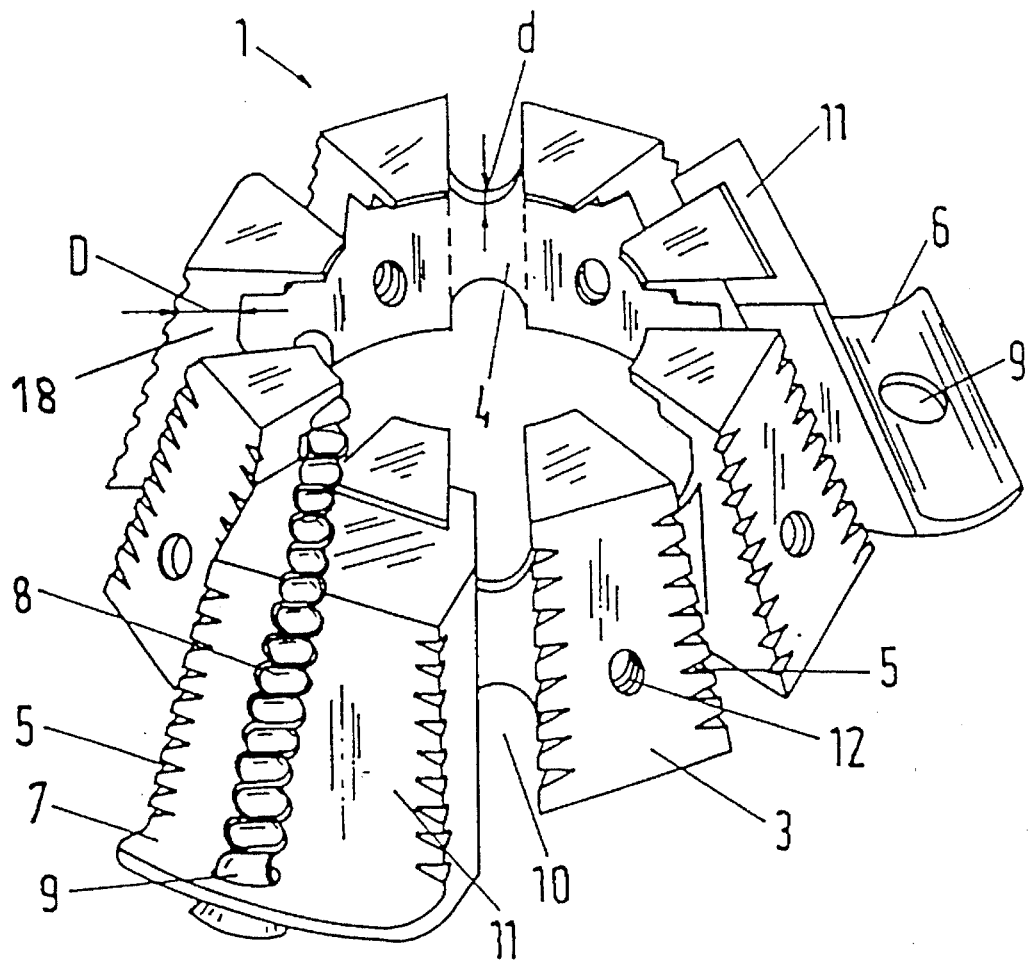
FIG. 1—shows in perspective a shell as the main body upon which two supporting bodies are fixed.

The shell 1 manufactured from metal, for example, titanium or a titanium alloy. In its basic form the shell is a truncated cone and includes of regions 3 of greater wall thickness D alternating in the circumferential direction with regions 4 of less wall thickness d, which form sectors of a circular ring with parallel walls. The regions 4 also include recesses 10 from both endfaces of the truncated cone, through which their flexibility is increased. The wall thickness D of the region 3 of greater wall thickness is measured along lateral surface 18.

As in the embodiment shown of a shell 1 this may furthermore be slit over its whole height along a directrix, likewise increasing the flexibility and elasticity of the shell 1.

Furthermore the regions 3 of greater wall thickness D are structured on the outside by a transverse set of teeth 5 in the circumferential direction. Bone tissue grows into the teeth and helps secure the joint.

The regions 8 of greater wall thickness D are trapezoidal in cross-section and converge cortically from the base of the truncated cone towards the pole whereby they form guideshoes for the supporting bodies 11 which embrace them like a dovetail and may be slid onto the regions 3 from the pole. The supporting bodies 11 are in that case advantageously adapted in length along a directrix in such a way to the shell 1 that with the supporting bodies 11 mounted the endfaces of both are at least approximately flush.

Figure 6:
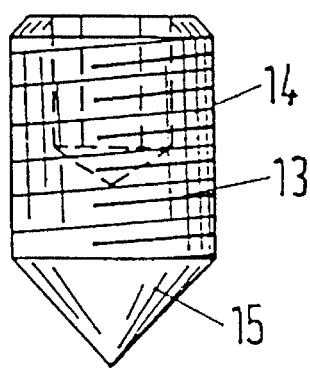
FIG. 6—shows on a larger scale an example of a setscrew serving as a fixing member.

A tapped hole 12 passes through each region 3 in the radial direction. A setscrew 13 is provided with a thread 14 (FIG. 6). The setscrew is screwed from the inside of the shell 1 as a fixing and centering member for a supporting body 11.

For exact positioning and centering of the supporting body 11 the setscrew 13 (FIG. 6) exhibits a centering tip 15 in the shape of a cone which penetrates into a hollow conical recess 16 (see, e.g., FIG. 2b) in a supporting body 11.

Figure 3A:
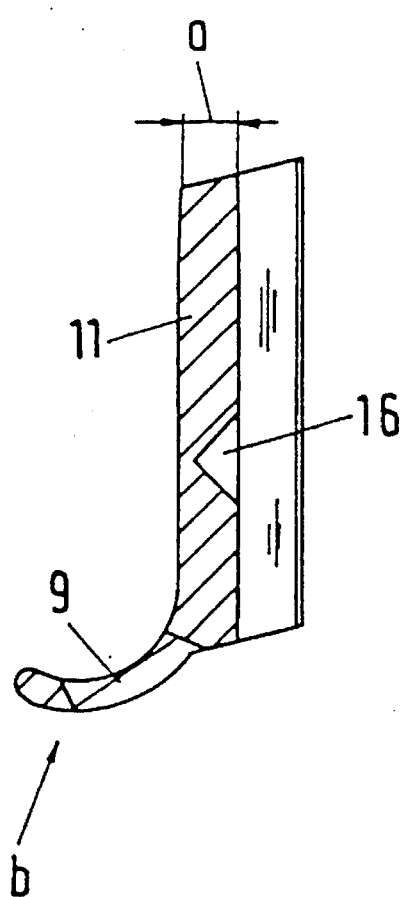
FIGS. 3a and 3b also 4a and 4b—are two further examples of different supporting bodies, 3a and 4a being the sections A—A from 3b and 4b respectively, whilst these two part Figures represent views corresponding with FIG. 2c.
Figure 5A:
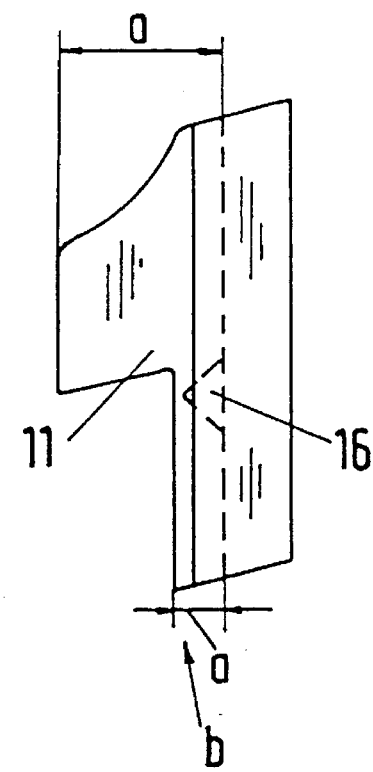
FIGS. 5a and 5b—are representations of a further supporting body, corresponding with FIGS. 2a and 2c.

As already mentioned a whole number of supporting bodies 11 of different dimensions and shapes may be associated with each shell 1. The simplest supporting body 11 (FIG. 2) is a rectangular body which is likewise of trapezoidal cross section; from this body a recess 17 is machined like a dovetail (FIG. 2b) which in shape and dimensions is adapted with a small play due to tolerances to the region of greater wall thickness D or the guideshoe 8 on the shell 1, and by which the supporting body 11 embraces the guideshoe. The differing thickness in the direction radial to the various supporting bodies 11—compare, for example, FIGS. 3a and 4a—is designated by a in all of the examples.

Figure 3B:
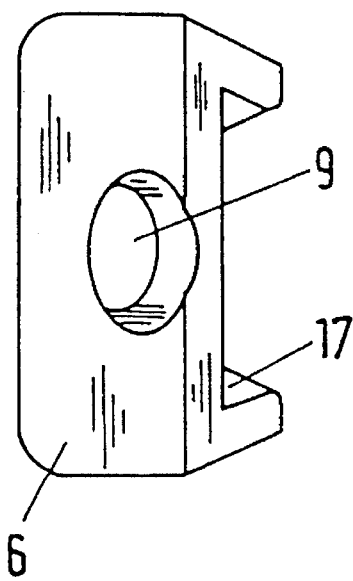
Figure 5B:
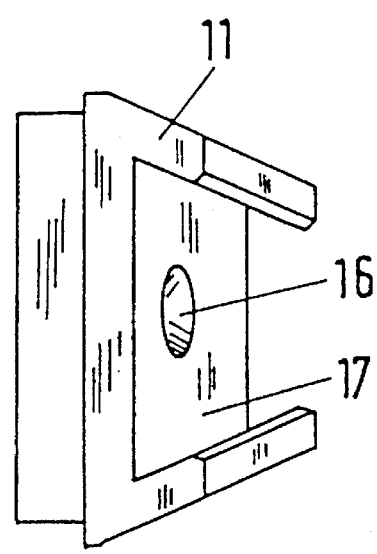

In the case of the supporting body according to FIG. 3 the simple shape according to FIG. 2 is completed at the endface next the base by a flap 6 having a slightly arched shape. A drilled hole 9 is provided in the flap 6 for a bone screw 8 to pass through (FIG. 1).

The supporting body 11 according to FIG. 4 differs from the two above, firstly by its greater thickness and secondly by its flap 7—which likewise exhibits a drilled hole 9—being plane and set at an angle from the supporting body 11 differing from the flap 6.

In the last example of a supporting body 11 shown its thickness a in the radial direction is not constant over the height of its surface but reduced in the form of a step, the greater thickness with the supporting body mounted coming to lie towards the pole side of the truncated cone of the shell 1.

Like the surfaces of the regions 3 of the shell 1 the surfaces of the supporting bodies 11 may also be provided with a transverse set of teeth 5 (FIG. 1) in order to promote the growth of bone tissue onto and/or into them.

Obviously both for the supporting bodies and also for their connection to the shell and for their fixing and centering other shapes and constructions are possible such, as for example, as double flaps or other shapes adapted to the individual conditions of the acetabulum.

We claim:

1. A hipjoint socket for anchoring in the pelvic bone, comprising:

at least one supporting body;

a frustoconical shell made of metal and having a hollow inside, the shell also having regions of greater wall thickness alternating in a circumferential direction with regions of lesser wall thickness, the regions of lesser wall thickness having a cross-section in the form of sectors of a circular ring, the regions of greater wall thickness having a cross-section which is essentially trapezoidal and tapers conically towards a pole, the regions of greater wall thickness having guideshoes extending along the outer surface, the regions of greater wall thickness having means for fixing the supporting body to the shell;

an insert having a cup of the socket, the insert being sized for a snug fit in the hollow inside; and the supporting body being adapted to engage at least one of said guideshoes, wherein the supporting body has a recess having a dovetail shape which engages the trapezoidal cross-section of the regions of greater wall thickness and may be slipped onto the guideshoes from the pole.

2. A hipjoint socket as in claim 1, further comprising:

a setscrew having a conical centering tip;

the regions of greater wall thickness having a hole therethrough, the setscrew being positioned in the hole; and the supporting body having a conical shaped recess, the conical shaped recess receiving the conical centering tip of the setscrew.

3. A hipjoint socket as in claim 1, wherein:

the supporting body has a thickness in a radial direction which increases towards the pole in the form of a step.

4. A hipjoint socket for anchoring in the pelvic bone, comprising:

a frustoconical shell having a hollow inside, an outer surface, and regions of greater wall thickness alternating in a circumferential direction with regions of lesser wall thickness, the regions of greater wall thickness comprising guideshoes extending along the outer surface, the guideshoes having first and second lateral surfaces, the shell tapering conically towards a pole end; and at least one supporting body adapted to engage at least one guideshoe, the supporting body being positioned over at least a portion of the outer surface when the supporting body engages the at least one guideshoe, the supporting body being configured to slidably engage at least a part of the lateral surfaces of the guideshoes from the pole end of the shell.

5. A hipjoint socket as in claim 4, further comprising a second supporting body having a different shape than said first supporting body.

6. A hipjoint socket as in claim 5, wherein at least one of said supporting bodies comprise a flap extending outwardly from an end thereof.

7. A hipjoint socket as in claim 4, wherein said body supporting has a base at one end thereof, a thickness of the supporting body changing steadily in a radial direction from said base.

8. A hipjoint socket as in claim 4, wherein the regions of greater wall thickness include transverse teeth.

9. A hipjoint socket as in claim 4 wherein:

the frustoconical shell comprises an axis of symmetry; and the regions of greater wall thickness have a generally trapezoidal cross-sectional shape transverse to the axis of symmetry.

10. A hipjoint socket as in claim 4, further comprising:

a setscrew having a conical centering tip;

the regions of greater wall thickness having a hole therethrough, the setscrew being positioned in the hole; and the supporting body having a conical shaped recess, the conical shaped recess receiving the conical centering tip of the setscrew.

11. A hipjoint socket as in claim 4, wherein:

the supporting body has a thickness in a radial direction which increases towards the pole in the form of a step.

12. A hipjoint socket for anchoring in the pelvic bone, comprising:

at least one supporting body;

a frustoconical shell made of metal and having a hollow inside, the shell also having regions of greater wall thickness alternating in a circumferential direction with regions of lesser wall thickness, the regions of lesser wall thickness having a cross-section in the form of sectors of a circular ring, the regions of greater wall thickness having a cross-section which is essentially trapezoidal and tapers conically towards a pole, the regions of greater wall thickness having guideshoes extending along the outer surface, the regions of greater wall thickness having means for fixing the supporting body to the shell, the fixing means comprising a setscrew having a conical centering tip and a hole extending completely through at least one of said regions of greater wall thickness, the supporting body being adapted to engage at least one of said guideshoes, the setscrew passing though the hole and engaging the supporting body, the setscrew configured to be tightened from the hollow inside; and an insert having a cup of the socket, the insert being sized for a snug fit into the hollow inside the shell.

13. A hipjoint socket as in claim 12, wherein the setscrew engages the supporting body in a hollow conical recess adapted to engage the centering tip.

14. A hipjoint socket for anchoring in the pelvic bone, comprising:

at least one supporting body;

a frustoconical shell made of metal and having a hollow inside, the shell also having regions of greater wall thickness alternating in a circumferential direction with regions of lesser wall thickness, the regions of lesser wall thickness having a cross-section in the form of sectors of a circular ring, the regions of greater wall thickness having a cross-section which is essentially trapezoidal and tapers conically towards a pole, the regions of greater wall thickness having guideshoes extending along the outer surface, the guideshoes having first and second lateral surfaces;

an insert having a cup of the socket, the insert being sized for a snug fit in the hollow inside of said shell; and the supporting body being adapted to engage at least one of said guideshoes, the supporting body configured to engage at least a part of the outer and lateral surfaces.

\* \* \* \* \*